United States Patent
LaViolette et al.

(10) Patent No.: US 8,666,478 B2
(45) Date of Patent: Mar. 4, 2014

(54) METHOD FOR DETERMINING LOCATIONS OF IMPLANTED ELECTRODES WITH MEDICAL IMAGES

(75) Inventors: Peter S. LaViolette, Wauwatosa, WI (US); Scott D. Rand, Brookfield, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 49 days.

(21) Appl. No.: 13/500,207

(22) PCT Filed: Oct. 8, 2010

(86) PCT No.: PCT/US2010/051946
§ 371 (c)(1),
(2), (4) Date: Jun. 28, 2012

(87) PCT Pub. No.: WO2011/044442
PCT Pub. Date: Apr. 14, 2011

(65) Prior Publication Data
US 2012/0271151 A1    Oct. 25, 2012

Related U.S. Application Data

(60) Provisional application No. 61/249,660, filed on Oct. 8, 2009.

(51) Int. Cl.
*A61B 5/05* (2006.01)
(52) U.S. Cl.
USPC ........... 600/424; 600/407; 600/410; 382/128; 382/131
(58) Field of Classification Search
USPC ................ 600/407–429; 382/128–132
See application file for complete search history.

(56) References Cited

U.S. PATENT DOCUMENTS

| | | | | |
|---|---|---|---|---|
| 5,843,093 A * | 12/1998 | Howard, III | .................. | 606/130 |
| 6,129,685 A * | 10/2000 | Howard, III | .................. | 600/585 |
| 6,263,225 B1 * | 7/2001 | Howard, III | .................. | 600/378 |
| 6,330,466 B1 * | 12/2001 | Hofmann et al. | ............. | 600/378 |
| 6,567,690 B2 * | 5/2003 | Giller et al. | .................... | 600/473 |
| 6,591,004 B1 | 7/2003 | Vanessen et al. | | |
| 6,856,830 B2 * | 2/2005 | He | ................................ | 600/513 |
| 7,077,822 B1 * | 7/2006 | Howard, III | ............... | 604/93.01 |
| 7,346,382 B2 * | 3/2008 | McIntyre et al. | ............. | 600/407 |
| 7,941,202 B2 * | 5/2011 | Hetke et al. | ................... | 600/377 |
| 8,406,890 B2 * | 3/2013 | Goetz | ............................. | 607/59 |
| 8,538,537 B2 * | 9/2013 | Hulvershorn et al. | .......... | 607/45 |

(Continued)

OTHER PUBLICATIONS

The International Search Report and Written Opinion for International Application No. PCT/US2010/051946 with a mailing date of Dec. 9, 2010.

*Primary Examiner* — Sanjay Cattungal
(74) *Attorney, Agent, or Firm* — Quarles & Brady, LLP (57) ABSTRACT

A method for accurate localization and visualization of implanted electrodes, such as implanted intracranial electrodes, is provided. More particularly, a realistic representation of intracranial electrode positions on patient-specific post-implantation MRI brain renderings is obtained. The resulting computer models provide an accurate depiction of electrode locations on three-dimensional brain renderings that are suitable for use in surgical planning of resection boundaries around, for example, epileptic zones. Electrodes placed inter-hemispherically are also visible with this method. In addition, a method for creating electrode "shadows" cast upon the brain model surface is provided. These electrode shadows are useful for estimating cortical areas sampled by iEEG and for locating electrodes that may straddle sulci and contact two adjacent cortical gyri.

20 Claims, 5 Drawing Sheets

(56) References Cited

U.S. PATENT DOCUMENTS

| | | | |
|---|---|---|---|
| 2002/0045832 A1* | 4/2002 | Giller et al. | 600/473 |
| 2004/0006274 A1* | 1/2004 | Giller et al. | 600/473 |
| 2005/0055035 A1* | 3/2005 | Cosman et al. | 606/130 |
| 2005/0070781 A1 | 3/2005 | Dawant et al. | |
| 2005/0101855 A1 | 5/2005 | Miga et al. | |
| 2007/0167724 A1 | 7/2007 | Gadagkar et al. | |
| 2008/0097187 A1 | 4/2008 | Gielen et al. | |
| 2008/0154341 A1* | 6/2008 | McIntyre et al. | 607/59 |
| 2009/0196471 A1 | 8/2009 | Goetz et al. | |
| 2012/0101552 A1* | 4/2012 | Lazarewicz et al. | 607/62 |
| 2012/0116211 A1* | 5/2012 | McIntyre et al. | 600/416 |

\* cited by examiner

METHOD FOR DETERMINING LOCATIONS OF IMPLANTED ELECTRODES WITH MEDICAL IMAGES

CROSS-REFERENCE TO RELATED APPLICATIONS

This application represents the U.S. National Stage of International Application No. PCT/US2010/051946, filed Oct. 8, 2010 which claims the benefit of U.S. Provisional Patent Application Ser. No. 61/249,660 filed on Oct. 8, 2009, and entitled "Method for Determining Locations of Intracranial Electroencephalography Electrodes with Medical Images."The foregoing applications are incorporated herein by reference in their-entirety.

FIELD OF THE INVENTION

The field of the invention is medical imaging systems and methods. More particularly, the invention relates to determining and visualizing the locations of implanted intracranial electrodes using a first set of post-implantation images, for example, acquired using magnetic resonance imaging ("MRI") and a second set of post-implantation images, for example, images acquired using x-ray computed tomography ("CT").

BACKGROUND OF THE INVENTION

Subdural electrodes are placed on the brains of patients in a range of different medical procedures. For example, epileptic patients with medically intractable, that is, drug-resistant, seizure disorders are often evaluated for possible surgical therapy. Most surgical candidates are subject to implantation of subdural metallic electrodes upon the brain surface, or depth electrodes with tips beneath the brain surface, for the purpose of seizure localization by intracranial electroencephalography ("iEEG") and for mapping of eloquent cortex. Planning surgical margins for resection of epileptic zones is a challenging problem due to the uncertainty associated with subdural electrode positions and inaccurate, labor-intensive techniques for electrode localization. Several techniques have been employed to visualize electrode placement in vivo including metal artifact localization, such as those methods described by M. A. Silberbusch, et al., in "Subdural Grid Implantation for Intracranial EEG Recording: CT and MR Appearance," *AJNR Am. J. Neuroradiol.*, 1998; 19:1089-1093; three-dimensional reconstruction and x-ray derived location projection, such as those methods described by P. A. Winkler, et al., in Usefulness of 3-D Reconstructed Images of the Human Cerebral Cortex for Localization of Subdural Electrodes in Epilepsy Surgery," *Epilepsy Res.*, 2000; 41:169-178; and automated template MRI transformation and projection, such as those methods described by D. Kovalev, et al., in "Rapid and Fully Automated Visualization of Subdural Electrodes in the Presurgical Evaluation of Epilepsy Patients," *AJNR Am. J. Neuroradiol.*, 2005; 26:1078-1083.

Additional methods to visualize electrode placement include x-ray co-registration, such as those methods described by K. J. Miller, et al., in "Cortical Electrode Localization from X-Rays and Simple Mapping for Electrocorticographic Research: The 'Location on Cortex' (LOC) Package for MATLAB," *J. Neurosci. Methods*, 2007; 162:303-308; curvilinear reformation, such as those methods described by A. H. Schulze-Bonhage, et al., in "Visualization of Subdural Strip and Grid Electrodes Using Curvilinear Reformatting of 3D MR Imaging Data Sets," *AJNR Am. J. NeuroradioL*, 2002; 23:400-403; and CT/MRI image co-registration, such as those methods described by R. Grzeszczuk, et al., in "Retrospective Fusion of Radiographic and MR Data for Localization of Subdural Electrodes," *J. Comput. Assist. Tomogr.*, 1992; 16:764-773, by M. Nelles et al., in "Fusion of MRI and CT with Subdural Grid Electrodes," *Zentralbl. Neurochir.*, 2004; 65:174-179, and by J. X. Tao, et al., in "The Accuracy and Reliability of 3D CT/MRI Co-Registration in Planning Epilepsy Surgery," *Clin. Neurophysiol.*, 2009; 120:748-753.

Moreover, methods for visualizing electrode placement also include computer aided stereotactic model creation, such as those methods described by K. Morris, et al., in "A Computer-Generated Stereotactic 'Virtual Subdural Grid' to Guide Resective Epilepsy Eurgery," *AJNR Am. J. Neuroradiol.*, 2004; 25:77-83; and digital 2D photography co-registered to 3D reconstructed MRI, such as those methods described by M. Mahvash, et al., in "Coregistration of Digital Photography of the Human Cortex and Cranial Magnetic Resonance Imaging for Visualization of Subdural Electrodes in Epilepsy Surgery," *Neurosurgery*, 2007; 61:340-344, discussion 344-345, and by J. Wellmer, et al., "Digital Photography and 3D MRI-Based Multimodal Imaging for Individualized Planning of Resective Neocortical Epilepsy Surgery," *Epilepsia*, 2002; 43:1543-1550. It is noted, however, that methods such as those disclosed by Morris, et al., rely on model creation using so-called virtual ray tracing approaches, in which a model of the cerebral surface is produced by effectively shining a light on the surface of the brain as depicted in post-implantation images. The noted limitation of such methods is that susceptibility artifacts resulting from the presence of implanted electrodes are pervasive in MR images, thereby yielding inaccurate cerebral models when ray tracing is implemented.

More recently, intra-operative fluoroscopy has been used for strip electrode placement, such as those methods described by L. Eross, et al., in "Neuronavigation and Fluoroscopy-Assisted Subdural Strip Electrode Positioning: a Simple Method to Increase Intraoperative Accuracy of Strip Localization in Epilepsy Surgery," *J. Neurosurg.*, 2009; 110: 327-331. These methods are useful in the visualization of grid and strip locations, but lack a degree of accuracy and/or resolution in imaging detail due to interpolation and projection limitations. Many of these techniques also rely on expert guidance and manual marking of electrode positions, making them prone to human measurement error.

Some of the more recently published procedures rely on 2D photographic information regarding electrode position. This introduces discrepancies in position through the estimation of complicated three-dimensional brain geometry with two-dimensional pictorial information. Also, only visible electrodes exposed by the craniotomy defect during the implantation of electrodes can be photographed in the operating room. Thus many electrodes cannot be localized by intra-operative photography, especially strip electrodes placed via small burr hole craniotomies. Most importantly, when the craniotomy defect is closed, brain distortion and cortical compression can physically shift electrodes from their initial photographed positions, as described in previous studies by D. L. Hill, et al., in "Measurement of Intraoperative Brain Surface Deformation Under a Craniotomy," *Neurosurgery*, 1998; 43:514-526, discussion 527-518. This compression affects the cortex at the critical period of patient monitoring by iEEG, making quantification of changes in the positioning of the brain and precise measurement of electrode positions following their implantation essential.

X-ray image projection corrects for this brain distortion when x-ray image acquisition follows the closure of the craniotomy defect; however, 2D x-ray images still require elaborate registration techniques for 3D visualization on cortical surfaces, such as those described by S. S. Dalai, et al., in "Localization of Neurosurgically Implanted Electrodes Via Photograph-MRI-Radiograph Coregistration," *J. Neurosci. Methods*, 2008; 174:106-115, and are not currently realizable without dedicated experts. The projection of x-ray data onto the brain surface requires a vertex point for back projection and manually defined landmarks. This method ultimately lacks 3D information required for visualizing foreshortened electrode strips oriented along the x-ray path rather than perpendicular to the x-ray beam, and lacks information for medially located electrodes.

Projection of electrode positions onto 3D renderings of brain MRI scans acquired prior to the implantation of the electrodes into the patient is also a common practice found in most previously published methods. Consider, for example, the methods described by S. S. Dalai, et al., in "Localization of Neurosurgically Implanted Electrodes Via Photograph-MRI-Radiograph Coregistration," *J. Neurosci. Methods*, 2008; 174:106-115, by J. D. Hunter, et al., in Locating Chronically Implanted Subdural Electrodes Using Surface Reconstruction," *Clin. Neurophysiol.*, 2005; 116:1984-1987, by M. Mahvash, et al., in "Coregistration of Digital Photography of the Human Cortex and Cranial Magnetic Resonance Imaging for Visualization of Subdural Electrodes in Epilepsy Surgery," *Neurosurgery*, 2007; 61:340-344, discussion 344-345, by K. J. Miller, et al., in "Cortical Electrode Localization from X-Rays and Simple Mapping for Electrocorticographic Research The 'Location on Cortex' (LOC) Package for MATLAB,"*J. Neurosci. Methods*, 2007; 162:303-308, and by M. Nelles et al., in "Fusion of MRI and CT with Subdural Grid Electrodes," *Zentralbl. Neurochir.*, 2004; 65:174-179. This is done because MRI images gathered post-implantation are subject to magnetic field susceptibility artifacts caused by the metal electrodes at the surface of the brain. 3D rendering of electrode-affected images has thus been limited, and subsequently brain shift and compression caused by electrode grids and craniotomy defects have never been addressed in imaging models. However, post-implantation MR images are necessary to visualize the cortical displacement and flattening that affect electrode position relative to the brain surface.

It would therefore be desirable to provide a method for the registration of iEEG electrode locations with a subject-specific 3D brain model that accounts for potential post-implantation brain shifts and is not negatively affected by susceptibility artifacts. Despite the numerous and varied technical solutions developed over a wide span of years, as described above in detail, none have yet been able to provide such a method.

SUMMARY OF THE INVENTION

The present invention overcomes the aforementioned drawbacks by providing a method for the registration of implanted electrode locations, such as implanted intracranial electroencephalography ("iEEG") electrode locations, with a subject-specific 3D brain model produced from post-implantation magnetic resonance ("MR") images of the subject. More particularly, a method is provided for the determination of the locations of such implanted intracranial electrodes. Subsequently, the locations are displayed on a three-dimensional rendering of a subject-specific, post-implantation cortical surface reconstruction. This rendering, or brain model, is produced using a method that begins with seed points located, for example, at the boundary between gray matter and white matter in 3D MR images, and then builds the model outward towards the cortical surface. This method utilizes the combination of post-implantation CT and MR imaging, and provides 3D representations of each subject's uniquely compressed, cortical surface anatomy with iEEG electrode locations overlaid. It also allows for midline cortical surface views of electrodes placed deep between the cerebral hemispheres in the interhemispheric fissure, previously unobtainable using whole-brain 3D volume rendering techniques. Additionally, a method is provided for creating illustrative electrode "shadows" that identify cortical patches beneath each electrode and help locate sulcal-straddling electrodes that potentially record iEEG signals from two adjacent gyri.

It is an aspect of the invention to provide a method for implanted electrode localization that augments or replaces current methods of stereotactic surgical planning. For example, a method for the simultaneous visualization of post-implant 2D MR images with CT overlay and a realistic 3D model of the combined modalities to depict subdural and/or depth electrodes is provided. In such a method, conventional axial, sagittal, and coronal image planes are yoked together to display deep brain structures.

It is another aspect of the invention to provide a method for implanted electrode localization that requires substantially no manual steps in determining electrode position. Instead, electrode locations are physically measured in co-registered CT images and overlaid on a subject-specific 3D model of the brain. This automation minimizes human error in producing reliable images for use in, for example, epilepsy surgery planning.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Surgical resection of cortical areas that initiate seizures can be an effective treatment option for patients with, for example, drug-resistant partial epilepsy. Intracranial electroencephalography ("iEEG") studies are often necessary for localizing seizure onset zones. These multichannel EEG tracings are traditionally analyzed visually to identify surgical targets. To acquire these tracing, subdural, or intracranial, electrodes are surgically implanted in the subject's brain. Exemplary electrodes include platinum-iridium alloy electrode discs (Ad-Tech Medical, Racine, Wis.) having a diameter, for example, of 4 millimeters ("mm"). Such exemplary electrodes are arranged in any number of particular arrangements, including, for example, a grid (e.g., 8×8), a partial grid (e.g., 8×2), and a strip (e.g., 4×1, 6×1, and 8×1). It should be appreciated by those skilled in the art that combinations of each of the preceding electrode arrangements are possible. Burr hole, or "trephine," craniotomies are performed for some strip electrode implantations. The subdural grids are sewn to the dura to prevent movement during inpatient seizure monitoring with continuous video-iEEG recording.

Figure 1:
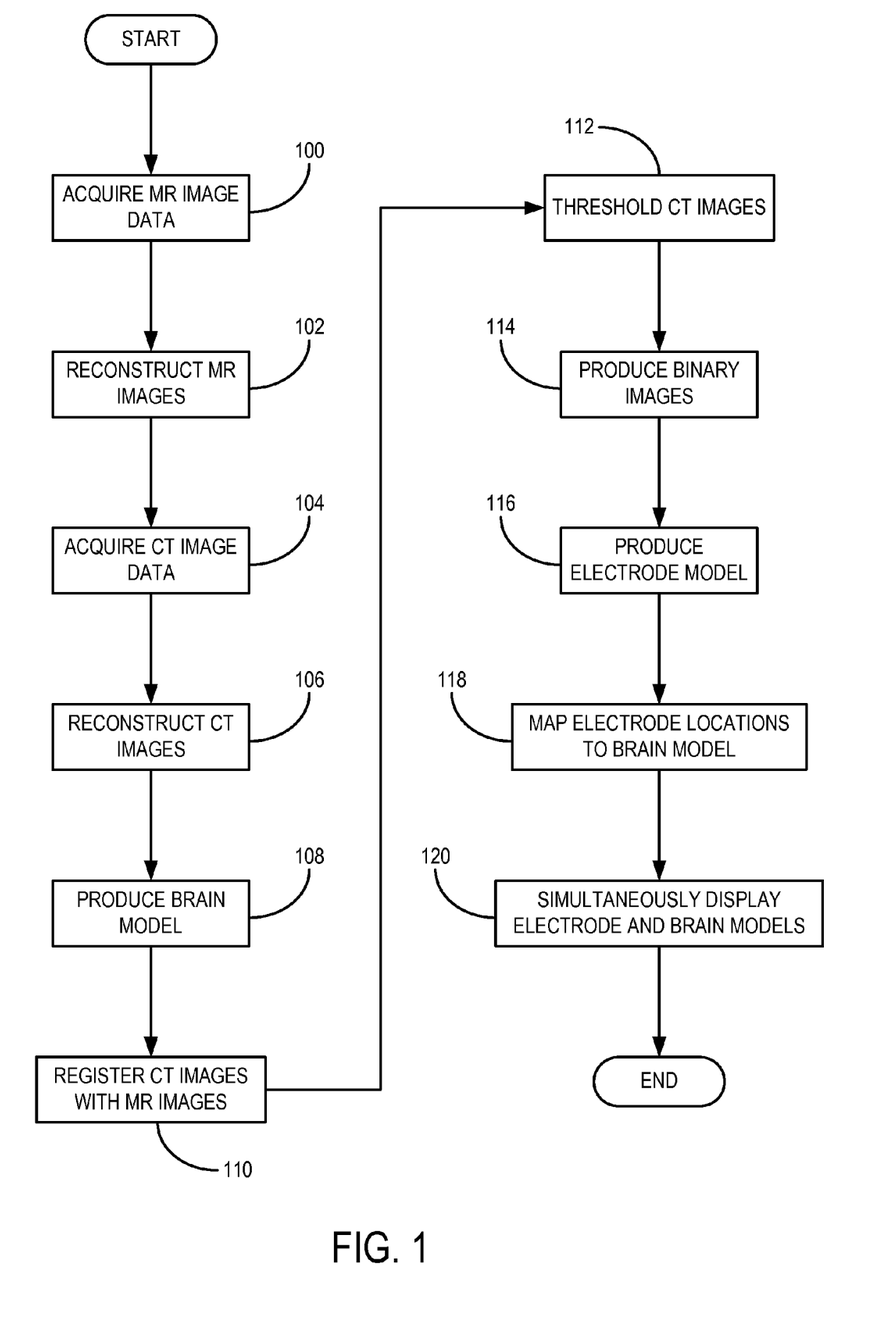
FIG. 1 is a flowchart setting forth the steps of an exemplary method for determining the location of an implanted electrode in a subject's brain in accordance with the present invention.

Referring now to FIG. 1, a flowchart setting forth the steps for performing a method of determining the locations of implanted electrodes on a subject's brain is shown. The method begins with the acquisition of MR image data from the subject, as indicated at step 100. This anatomical 3D MR image data is acquired by directing the MRI system to perform, for example, a $T_1$-weighted spoiled gradient echo ("SPGR") pulse sequence or a magnetization prepared rapid gradient echo ("MPRAGE") pulse sequence. From the acquired MR image data, anatomical MR images of the subject are reconstructed in the typical fashion, as indicated at step 102. While the anatomical MR image data is acquired after the implantation of the electrodes in the subject, additional medical image data can also be acquired prior to the surgical implantation of the electrodes. Exemplary additional medical image data include those acquired with $T_1$, $T_2$, $T_2^*$, and proton density weighted MRI; fluid attenuation inversion recovery ("FLAIR") MRI; diffusion weighted imaging ("DWI"); diffusion tensor imaging ("DTI"); perfusion weighted CT and MRI; functional MRI ("fMRI"); MR spectroscopy; positron emission tomography ("PET"); and single photon emission computed tomography ("SPECT"). The choice to acquire such additional medical image data is made as warranted by the desired surgical evaluation and plan. As will be described below in detail, such pre-implantation medical image data can be further included in a produced surgical plan by way of non-rigid (i.e., deformable) image co-registration, providing diagnostic information related to regions of the brain in proximity to potential resection zones.

In addition to acquiring post-operative MR image data, post-operative CT image data is also acquired from the subject, as indicated at step 104. The post-implant CT scan is performed with, for example, the CT imaging system described above. After the acquisition of the post-operative CT image data has completed, CT images are reconstructed in the typical fashion, as indicated at step 106. As will be described below in detail, the post-implant MR images are used to create a subject specific 3D model of the brain. This model includes structural changes resulting from, for example, compression of the brain during and after the surgical implantation of the electrodes. Additionally, the CT images are used for electrode localization by way of rigid, non-deformable co-registration to the post-implant MR images. Both the CT and MR images are acquired after surgical placement of the electrodes. It will be appreciated by those skilled in the art that the post-implantation images can be acquired in any number of clinically acceptable time windows following the implantation of the electrodes.

The subject-specific 3D brain model is a model of the subject's cortical surface, and is produced from the reconstructed post-operative MR images next, as indicated at step 108. The model is produced from the MR images using a method that builds the model starting at seed points within the brain, such as can be done using the software programs FreeSurfer (Athinoula A. Martinos Center for Biomedical Imaging, Massachusetts General Hospital, Boston, Mass.) or NeuroQuant® (CorTechs Labs, Inc., La Jolla, Calif.), which were designed to effectuate quantitative measurements of cortical thickness. For example, such methods may begin by segmenting the brain into white matter, gray matter, and cerebrospinal fluid ("CSF"). A surface is then wrapped around the segmented white matter volume and is smoothed so as to remove the step-like characteristic of the voxels' shape. At this instance, a triangular lattice surface is defined. Lines perpendicular to this surface are then followed outward from the surface until a steep intensity gradient related to the gray matter segmentation boundary is located. In this manner, such algorithms are viewed as building a model from "seed locations" on the white matter outward to the gray matter boundary.

Using methods such as these, an accurate cortical surface model is produced from MR images even in the presence of susceptibility artifacts generated by implanted metallic electrodes. More particularly, the commonly used methods for producing brain surface models from MR images for surgical planning rely on virtual ray tracing methods that first remove, or "strip," the skull from the MR images. These methods then build the model of the cortical surface by effectively "shining a light" on the skull stripped MR images. In this manner, a model of the cortical surface is produced by determining those locations where a ray intersects with the outermost portion of the intensity in the images, whether truly from the cortical surface or not. For example, in the presence of susceptibility artifacts generated by the implanted electrodes, these models are inaccurate since both the skull stripping method and the cortical surfaces generated by ray tracing will be distorted by the imaging artifacts.

On the contrary, using one of the aforementioned methods that work from the inside of the brain out, major sulcal and gyral patterns remain intact in a rendered model that is suited for interactive, computer-guided surgical planning. In addition, using such methods, each cerebral hemisphere is produced separately in the model, which allows the visualization of medial brain surfaces that are separated by the falx cerebri (i.e., dural brain covering) within the interhemispheric fissure. While this view is unobtainable with the commonly utilized photographic co-registration techniques and volume rendering methods that use virtual ray tracing to simulate reflected light from the whole brain surface in vivo, visualization of electrodes placed between the cerebral hemispheres is possible with the herein described method.

After the model of the subject's brain is produced, as described above, the locations of the implanted electrodes are determined using the reconstructed CT images. First, the CT images are co-registered to the post-implant MR images, as indicated at step 110. This is achieved, for example, using the software program FLIRT (Oxford Centre for Functional MRI of the Brain, University of Oxford, Oxford, England). Since the brain surface model is produced from these same reconstructed MR images, this step inherently co-registers the CT images with the corresponding locations within the brain surface model as well. The CT data is then intensity thresholded to produce images showing substantially only the highly attenuating electrodes, as indicated at step 112. The threshold value is selected to substantially suppress streak, or "beam hardening," artifacts produced by the metallic electrodes. However, it will be appreciated by those skilled in the art that alternate methods for image segmentation or pattern recognition can be employed to localize the electrodes in the reconstructed CT images. From these thresholded CT images, binary images are produced next, as indicated at step 114. In this manner, so-called "electrode images" are produced that contain substantially only information corresponding to the measured CT signal from the locations of the implanted electrodes. For example, the produced binary images contain clusters of pixels, or 3D voxels, having binary values of one in those locations where an electrode is present in the original CT images, and will have binary pixel values of zero elsewhere. 3D electrode models are then created using the binary images in a similar format to the 3D brain surface model, as indicated at step 116.

Both the produced 3D model of the subject's brain surface and the produced 3D model of the binary electrodes alone are then visualized together simultaneously. Moreover, the locations of the implanted electrodes are mapped onto the brain surface model, as indicated at step 118. In this manner, brain model surface based "electrode shadows" are created as additional indicators of proximal cortical sampling beneath the 3D electrode models. The creation of these brain surface-based electrode shadows begins, for example, by three-dimensional smoothing of the binary CT electrode images with a Gaussian filter having, for example, a 2 mm radius. Pial brain surfaces derived from the brain model are then partially inflated in a stepwise manner looking for intersections with the binary CT electrodes. This is achieved, for example, using a binary dilation operation. Any intersections between the inflated pial surfaces and the binary CT electrodes are recorded. Intersected values are then projected onto the brain model surface to indicate the locations on the brain surface that are coupled to the respective electrodes. The produced electrode and brain surface models are subsequently displayed in an overlay so that they can be viewed simultaneously, as indicated at step 120.

Projecting electrode shadows to the brain surface provides an illustrative tool for locating electrodes straddling a sulcus before neurosurgeons are faced with them in the operating room, for example, at the time of epileptic zone resection. Based on proximity alone, these sulcal-straddling electrodes potentially record iEEG signals from two different gyri, which potentially confound seizure onset localization, interpretation, and surgical planning. Visualization of the projected electrode locations on the produced brain model is achieved, for example, using a software program such as 3D Slicer (Brigham and Women's Hospital, Boston, Mass.). By combining the produced 3D model of the brain with the display of the projected electrode locations in the foregoing manner, a real-time, operator-guided rotational viewing of the combined 3D model of the brain surface rendering with orbiting electrodes and simultaneous traditional 2D coronal, sagittal, and axial views is provided. This display offers a synergy of many pieces of information, providing an advantageous tool for surgical planning. Data measured from the electrodes, for example, time-dependent iEEG recordings, can be painted onto the 3D brain surface model for further anatomical analysis as a video clip of "iEEG shadows." This can be achieved, for example, using a boundary element method ("BEM"), finite element method ("FEM"), or projection via electrode shadow location.

Figure 2:
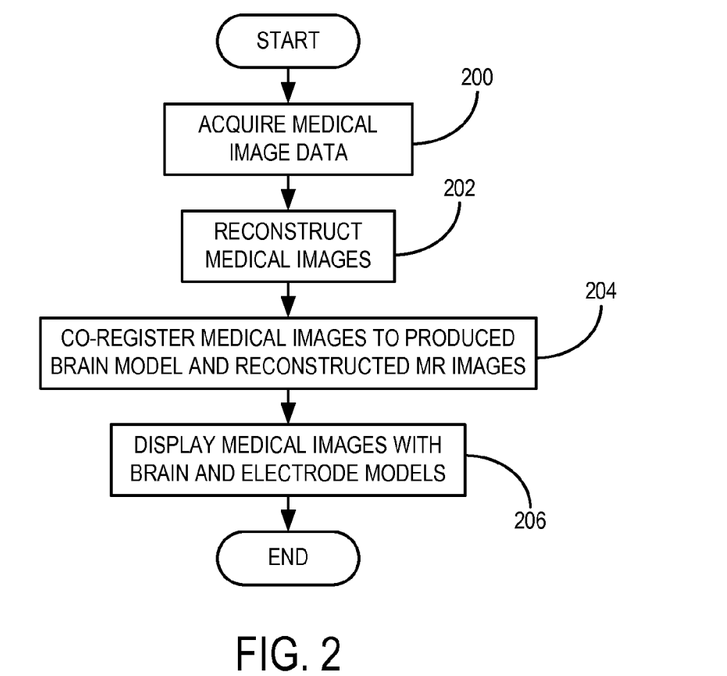
FIG. 2 is a flowchart setting forth the steps of an exemplary method for overlaying medical images with model of implanted electrodes and the surface of a subject's brain in accordance with the present invention.

Additional information can similarly be displayed with the produced brain surface and electrode models. Referring now to FIG. 2, a flowchart setting forth the steps for performing an exemplary method of incorporating such additional information is shown. First, additional medical image data is acquired from the subject, as indicated at 200. As described above, exemplary additional medical image data include those acquired with $T_1$, $T_2$, $T_2^*$, and proton density weighted MRI; fluid attenuation inversion recovery ("FLAIR") MRI; diffusion weighted imaging ("DWI"); diffusion tensor imaging ("DTI"); perfusion weighted CT and MRI; functional MRI ("fMRI"); MR spectroscopy; positron emission tomography ("PET"); and single photon emission computed tomography ("SPECT"). The choice to acquire such additional medical image data is made as warranted by the desired surgical evaluation and plan. From this additional medical image data, medical images are reconstructed, as indicated at step 202. As indicated at step 204, these reconstructed medical images are then co-registered with the post-implantation MR images reconstructed at step 102 and the brain surface model produced at step 108. This co-registration is accomplished, for example, by way of a rigid or non-rigid, deformable image co-registration methods. After the co-registration, the medical images can be simultaneously displayed with the produced brain surface and electrode models, as indicated at step 206. In this manner, any number of relevant medical imaging information can be displayed with the produced brain surface and electrode models.

Thus, the herein described method provides numerous advances in subdural electrode localization and 3D modeling. This is achieved, in part, by the reconstruction and rendering of cortical brain models using MR images acquired after iEEG electrodes have been placed on the brain. This method accounts for cortical compression and brain shift caused by surgery and the presence of electrode grids. In addition, the brain model is produced using a method that builds from starting locations within the brain outward towards the cortical surface. For example, seed point locations are selected along the boundary between gray and white matter in the post-implantation MR images and an intensity gradient method is employed to build the model out towards the cortical surface. The herein described method also allows visualization of medially placed electrodes. Additionally, electrodes that straddle two or more sulci are detected prior to resective surgery, allowing for more accurate surgical planning. Thus, the herein described 3D modeling technique provides neurosurgeons and other clinicians the ability to more precisely determine the locations of implanted electrodes. As discussed above, the implanted electrode locations on the cortex are measured in the post-implantation state, which accommodates significant amounts of cortical flattening and distortion due to craniotomy defects. Until now, it has not been possible to accurately measure the effects of cortical displacement on electrode position in 3D models.

Because the produced cortical surface model is generated by starting at the juxtaposition between gray and white matter, the brain surface model is generally "hollow." Despite the added benefits of such a model in terms of improved electrode localization accuracy, such a model is not readily importable to surgical planning and navigation systems, such as the StealthStation® S7® surgical navigation system (Medtronic, Inc., Minneapolis, Minn.) and StealthStation® i7® integrated surgical navigation system (Medtronic, Inc., Minneapolis, Minn.). However, the model can be further processed so that this importability is provided.

Figure 3:
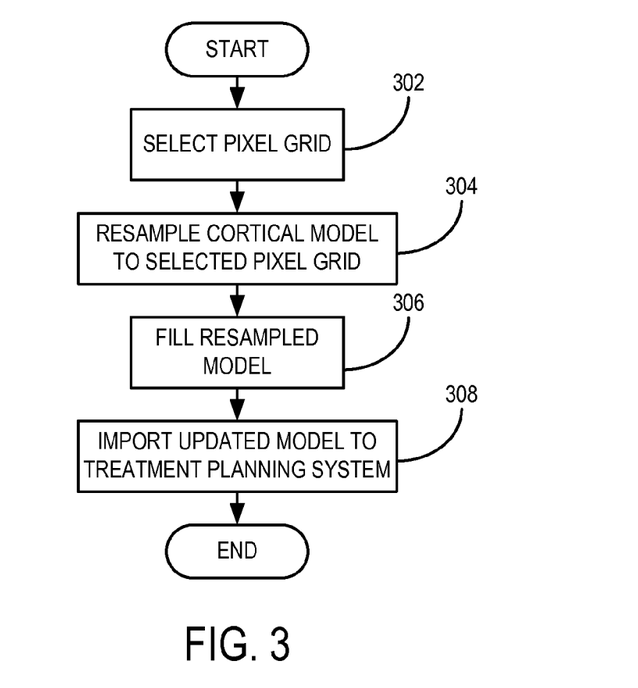
FIG. 3 is a flowchart setting forth the steps of an exemplary method for converting the generated cortical surface model into a brain model that is amenable to importation into a surgical navigation system.

Referring particularly now to FIG. 3, a flowchart setting forth the steps of an exemplary method for converting the produced cortical surface model into a model that is compatible with a surgical navigation system is illustrated. The method begins with the selection of a pixel grid, to which the cortical surface model is to be resampled, as indicated at step 300. The cortical surface is then resampled onto the selected pixel grid, as indicated at step 302. This resampling includes, for example, upsampling the cortical surface model to a finer resolution pixel grid. Accordingly, the pixel grid selected in step 300 may be a pixel grid with a resolution corresponding to a two-fold, four-fold, or other increase in resolution with respect to the resolution of the cortical surface model. Subsequently, the resampled model is "filled in," as indicated at step 304. As noted earlier, because the cortical model is generated from seed points located at the juxtaposition between gray and white matter, the model is generally hollow. Thus, to properly interface with a surgical navigation system, the model must be "filled in." This process is conducted, for example, by assigning pixel intensity values from the acquired post-implantation MR images to those associated pixel locations in the selected pixel grid that underlies the resampled cortical model. Alternatively, for example, unit binary values can be assigned to those locations within the cortical model and zero binary values to those locations outside of the cortical model. The method concludes with the importation of the resampled and filled, or "updated," model to the desired surgical navigation system, as indicated at step 306.

Figure 4A:
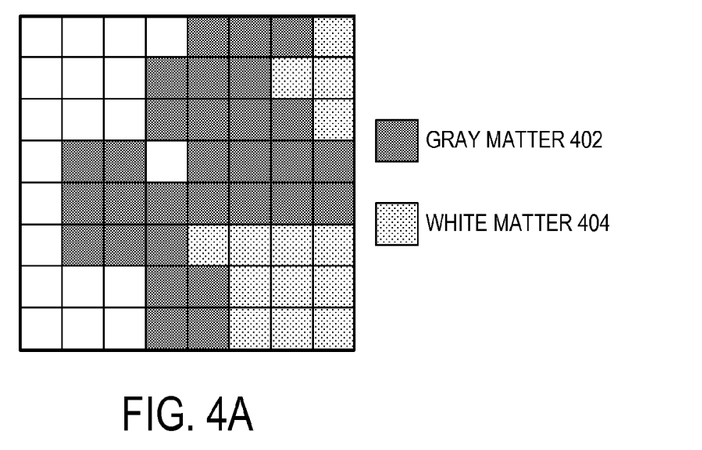
FIG. 4A is a pictorial representation of an exemplary segment of a post-implantation magnetic resonance image.
Figure 4B:
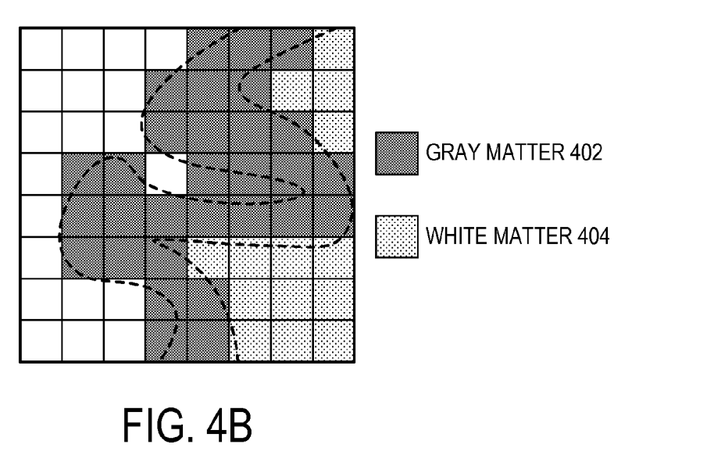
FIG. 4B is a pictorial representation of the exemplary segment of a post-implantation magnetic resonance image with gray matter and white matter segmentation boundaries overlaid thereon.
Figure 4C:
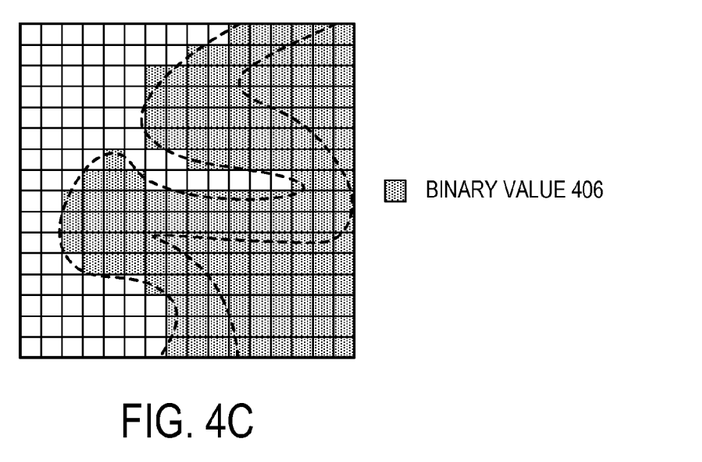
FIG. 4C is a pictorial representation of an exemplary two-dimensional segment of an updated brain model that is produced by resampling and filling a cortical surface model produced in accordance with embodiments of the invention.

By way of example, and referring now to FIGS. 4A-4C, a pictorial representation of the cortical surface model generation, resampling, and filling pixel locations within the cortical surface model is illustrated. Starting with a portion of a post-implantation MR image, such as the pictorial representation depicted in FIG. 4A, in which a juxtaposition between a gray matter area 402 and a white matter area 404 is depicted, a cortical surface model is generated. During the generation of the cortical surface model, the post-implantation MR image is segmented into gray matter, white matter, and cerebrospinal fluid regions. A two-dimensional example of such a segmented image is pictorially illustrated in FIG. 4B, in which the dashed lines indicate the surface-based boundaries between gray matter and white matter segmentation regions. After resampling, those pixel locations contained within the cortical surface model are assigned values, such as binary values 406 or image intensity values obtained from the post-implantation MR images. In FIG. 4C, a pictorial representation of an exemplary resampled and filled cortical surface model is depicted.

Figure 5:
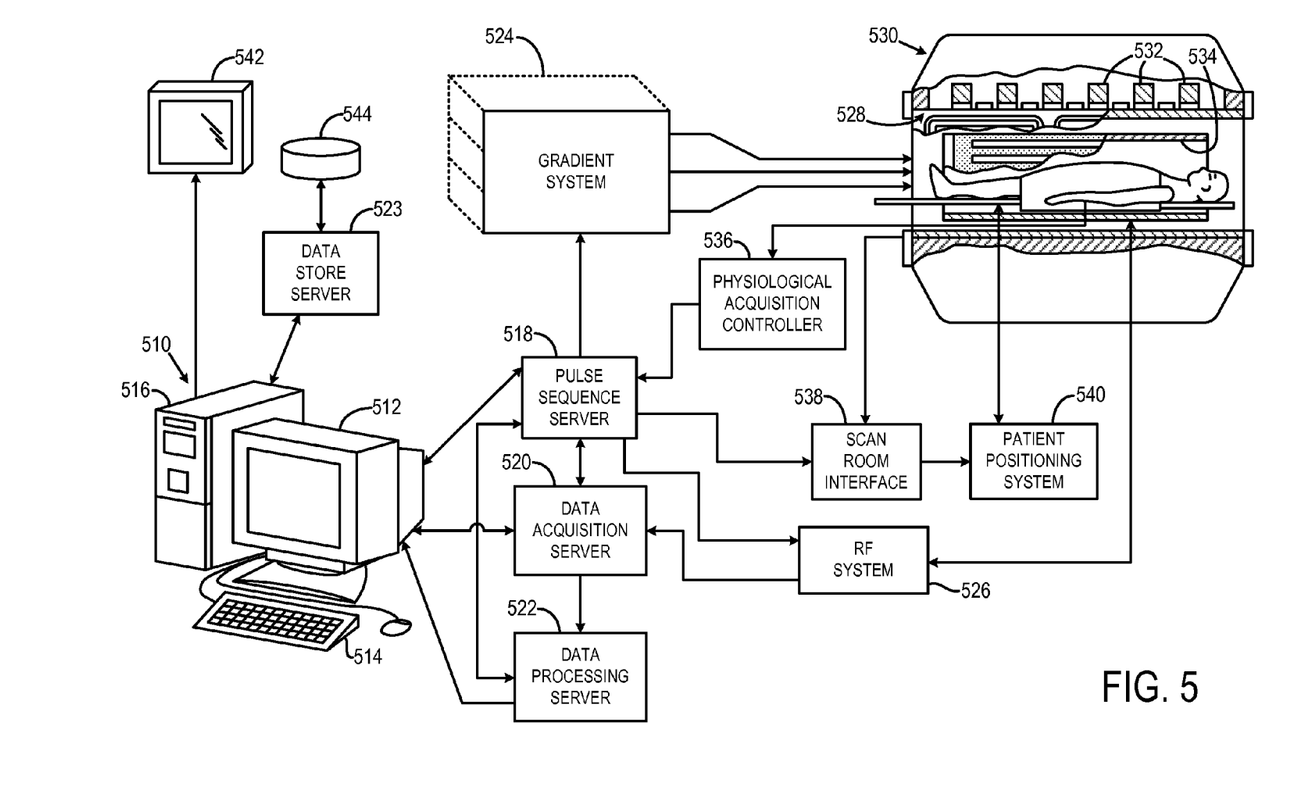
FIG. 5 is a block diagram of an exemplary magnetic resonance imaging ("MRI") system employed when practicing an embodiment of the present invention.

Referring particularly to FIG. 5, an exemplary magnetic resonance imaging ("MRI") system employed when practicing an embodiment of the present invention is shown. The MRI system includes a workstation 510 having a display 512 and a keyboard 514. The workstation 510 includes a processor 516 that is a commercially available programmable machine running a commercially available operating system. The workstation 510 provides the operator interface that enables scan prescriptions to be entered into the MRI system. The workstation 510 is coupled to four servers: a pulse sequence server 518; a data acquisition server 520; a data processing server 522, and a data store server 523. The workstation 510 and each server 518, 520, 522 and 523 are connected to communicate with each other.

The pulse sequence server 518 functions in response to instructions downloaded from the workstation 510 to operate a gradient system 524 and a radiofrequency ("RF") system 526. Gradient waveforms necessary to perform the prescribed scan are produced and applied to the gradient system 524 that excites gradient coils in an assembly 528 to produce the magnetic field gradients $G_x$, $G_y$, and $G_z$ used for position encoding MR signals. The gradient coil assembly 528 forms part of a magnet assembly 530 that includes a polarizing magnet 532 and a whole-body RF coil 534.

RF excitation waveforms are applied to the RF coil 534 by the RF system 526 to perform the prescribed magnetic resonance pulse sequence. Responsive MR signals detected by the RF coil 534 or a separate local coil (not shown in FIG. 5) are received by the RF system 526, amplified, demodulated, filtered and digitized under direction of commands produced by the pulse sequence server 518. The RF system 526 includes an RF transmitter for producing a wide variety of RF pulses used in MR pulse sequences. The RF transmitter is responsive to the scan prescription and direction from the pulse sequence server 518 to produce RF pulses of the desired frequency, phase and pulse amplitude waveform. The generated RF pulses may be applied to the whole body RF coil 534 or to one or more local coils or coil arrays (not shown in FIG. 5).

The RF system 526 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \tag{1},$$

and the phase of the received MR signal may also be determined:

$$\phi = \tan^{-1}\left(\frac{Q}{I}\right). \tag{2}$$

The pulse sequence server 518 also optionally receives patient data from a physiological acquisition controller 536. The controller 536 receives signals from a number of different sensors connected to the patient, such as ECG signals from electrodes or respiratory signals from a bellows. Such signals are typically used by the pulse sequence server 518 to synchronize, or "gate", the performance of the scan with the subject's respiration or heart beat.

The pulse sequence server 518 also connects to a scan room interface circuit 538 that receives signals from various sensors associated with the condition of the patient and the magnet system. It is also through the scan room interface circuit 538 that a patient positioning system 540 receives commands to move the patient to desired positions during the scan.

The digitized MR signal samples produced by the RF system 526 are received by the data acquisition server 520. The data acquisition server 520 operates in response to instructions downloaded from the workstation 510 to receive the real-time MR data and provide buffer storage such that no data is lost by data overrun. In some scans the data acquisition server 520 does little more than pass the acquired MR data to the data processor server 522. However, in scans that require information derived from acquired MR data to control the further performance of the scan, the data acquisition server 520 is programmed to produce such information and convey it to the pulse sequence server 518. For example, during prescans MR data is acquired and used to calibrate the pulse sequence performed by the pulse sequence server 518. Also, navigator signals may be acquired during a scan and used to adjust RF or gradient system operating parameters or to control the view order in which k-space is sampled. And, the data acquisition server 520 may be employed to process MR signals used to detect the arrival of contrast agent in a magnetic resonance angiography (MRA) scan. In all these examples the data acquisition server 520 acquires MR data and processes it in real-time to produce information that is used to control the scan.

The data processing server 522 receives MR data from the data acquisition server 520 and processes it in accordance with instructions downloaded from the workstation 510. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 522 are conveyed back to the workstation 510 where they are stored. Real-time images are stored in a data base memory cache (not shown) from which they may be output to operator display 512 or a display 542 that is located near the magnet assembly 530 for use by attending physicians. Batch mode images or selected real time images are stored in a host database on disc storage 544. When such images have been reconstructed and transferred to storage, the data processing server 522 notifies the data store server 523 on the workstation 510. The workstation 510 may be used by an operator to archive the images, produce films, or send the images via a network to other facilities.

Figure 6A:
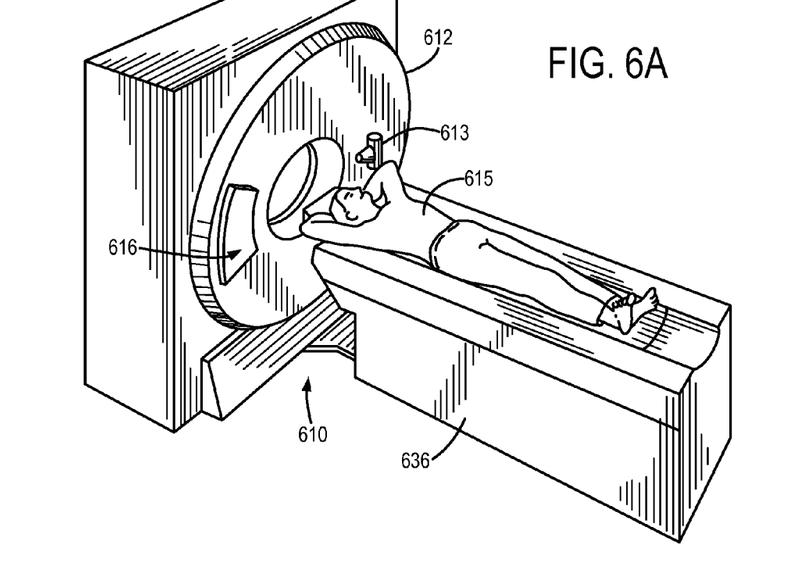
FIG. 6A is a perspective view of an exemplary computed tomography ("CT") imaging system employed when practicing an embodiment of the present invention.
Figure 6B:
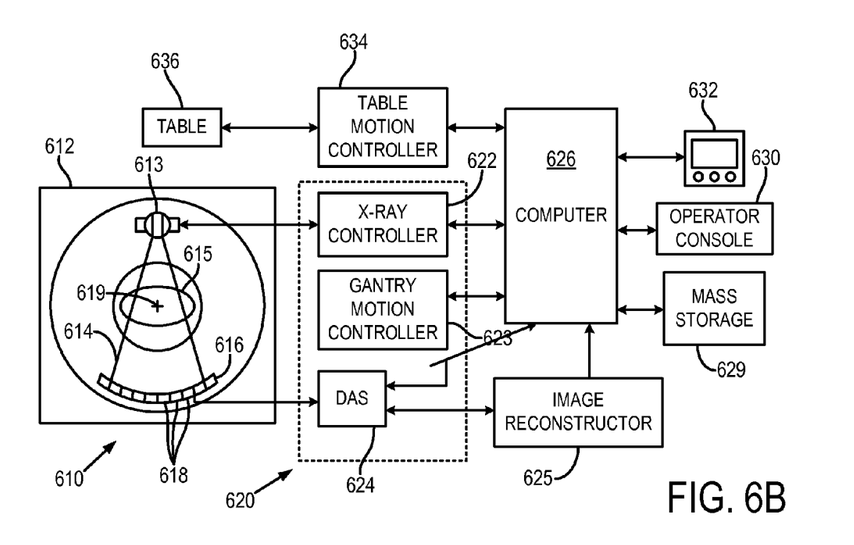
FIG. 6B is a block diagram of the CT imaging system of FIG. 6A.

An exemplary x-ray computed tomography ("CT") imaging system 610 employed when practicing an embodiment of the present invention, with initial reference to FIGS. 6A and 6B, includes a gantry 612 representative of a so-called "third generation" CT scanner. Gantry 612 has an x-ray source 613 that projects a fan-beam, or cone-beam, of x-rays 614 toward a detector array 616 on the opposite side of the gantry. The detector array 616 is formed by a number of detector elements 618 which together sense the projected x-rays that pass through a medical patient 615. Each detector element 618 produces an electrical signal that represents the intensity of an impinging x-ray beam and hence the attenuation of the beam as it passes through the patient. During a scan to acquire x-ray projection data, the gantry 612 and the components mounted thereon rotate about a center of rotation 619 located within the patient 615.

The rotation of the gantry and the operation of the x-ray source 613 are governed by a control mechanism 620 of the CT system. The control mechanism 620 includes an x-ray controller 622 that provides power and timing signals to the x-ray source 613 and a gantry motor controller 623 that controls the rotational speed and position of the gantry 612. A data acquisition system (DAS) 624 in the control mechanism 620 samples analog data from detector elements 618 and converts the data to digital signals for subsequent processing. An image reconstructor 625, receives sampled and digitized x-ray data from the DAS 624 and performs high speed image reconstruction. The reconstructed image is applied as an input to a computer 626 which stores the image in a mass storage device 628.

The computer 626 also receives commands and scanning parameters from an operator via console 630 that has a keyboard. An associated display 632 allows the operator to observe the reconstructed image and other data from the computer 626. The operator supplied commands and parameters are used by the computer 626 to provide control signals and information to the DAS 624, the x-ray controller 622 and the gantry motor controller 623. In addition, computer 626 operates a table motor controller 634 which controls a motorized table 636 to position the patient 615 in the gantry 612.

The present invention has been described in terms of one or more preferred embodiments, and it should be appreciated that many equivalents, alternatives, variations, and modifications, aside from those expressly stated, are possible and within the scope of the invention. For example, the complex source-modeling problem related to locating the precise anatomical origins of iEEG signals can be addressed when employing the herein described method of post-implantation MRI reconstruction and electrode location projection. Surgeons may also implant other diagnostic and/or therapeutic devices either beneath the skin or scalp, within the skull, beneath the skull in the epidural space, and/or beneath the dura in the subdural space. The location of such an implanted device relative to the brain surface can also be determined within the scope of the present invention, provided that the device can be isolated from CT or other medical images of the head by thresholding or other means of image segmentation or pattern recognition. For patients unable to undergo MRI, other medical imaging of the brain such as PET may substitute for MRI, albeit typically with lower image resolution.

The invention claimed is:

1. A method for determining a location of an electrode implanted in a subject's brain, the steps comprising:
    a) acquiring, with a magnetic resonance imaging (MRI) system, MR image data from the subject's brain;
    b) acquiring, with a computed tomography (CT) imaging system, CT image data from the subject's brain;
    c) reconstructing, from the acquired MR image data, MR images of the subject's brain;
    d) reconstructing, from the acquired CT image data, CT images of the subject's brain;
    e) producing from the reconstructed CT images, electrode images indicative of the location of the electrode;
    f) producing, from the reconstructed MR images, a model of the subject's brain by starting from a seed location within the brain and building the model outward to the surface of the brain; and
    g) mapping the location of the electrode onto the model of the subject's brain using the produced electrode images.

2. The method as recited in claim 1 in which step g) includes producing a three-dimensional model of the electrode using the produced electrode images.

3. The method as recited in claim 2 in which step g) includes dilating the model of the subject's brain and identifying an intersection between the dilated model of the subject's brain and the electrode model.

4. The method as recited in claim 2 further comprising:
    h) simultaneously displaying the model of the subject's brain and the three-dimensional model of the electrode.

5. The method as recited in claim 1 in which step g) includes:
    g)i) dilating model of the subject's brain; and
    g)ii) identifying an intersection between the dilated model of the subject's brain and the location of the electrode in the electrode image.

6. The method as recited in claim 1 in which the seed location within the brain is selected in step f) as a point lying on a boundary between gray matter and white matter.

7. The method as recited in claim 1 in which step f) includes producing the model by following an intensity gradient outward from the seed location towards the surface of the brain.

8. The method as recited in claim 1 in which step e) includes thresholding the reconstructed CT images using a preselected threshold value.

9. The method as recited in claim 1 in which the electrode images produced in step e) are binary images in which pixels corresponding to the implanted electrode have binary values of at least one of unity and a non-unitary binary value.

10. The method as recited in claim 1 further including:
   h) acquiring, with a medical imaging system, medical image data from the subject; and
   i) displaying information from the medical image data on the model of the subject's brain.

11. The method as recited in claim 10 in which the medical imaging system is an MRI system, the medical image data is functional MR image data, and step i) includes:
   determining information indicative of neuronal activity from the functional MR image data; and
   displaying the determined information indicative of neuronal activity on the produced model of the subject's brain.

12. The method as recited in claim 11 in which step i) includes mapping the determined information indicative of neuronal activity from pre-implantation locations in the subject's brain to post-implantation locations in the subject's brain.

13. The method as recited in claim 10 in which the medical imaging system is an electroencephalography (EEG) system in communication with the electrode, the medical image data is EEG data, and step i) includes:
   determining information indicative of neuronal activity from the EEG data;
   projecting the determined information onto the produced model of the subject's brain; and
   displaying the projected information indicative of neuronal activity on the produced model of the subject's brain.

14. The method as recited in claim 1 in which steps a) and b) are performed after the electrode has been implanted in the subject's brain.

15. The method as recited in claim 14 in which steps a)-g) are repeated around three to five days after implanting the electrode in the subject's brain in order to determine a new location of the electrode that accounts for structural changes in the subject's brain since implanting the electrode.

16. The method as recited in claim 1 further comprising importing the model into a surgical planning system.

17. The method as recited in claim 16 in which prior to importing the model into the surgical planning system the model is at least one of resampled and filled.

18. The method as recited in claim 17 in which resampling the model includes:
   i) defining a finer pixel gird; and
   ii) assigning an image intensity value of a pixel in the model to respective pixel locations in the finer pixel grid.

19. The method as recited in claim 17 in which filling the model includes:
   i) selecting a pixel grid; and
   ii) assigning an image intensity value of pixels in the reconstructed MR images to respective pixel locations in the finer pixel grid that substantially overlap with the pixel locations in the reconstructed MR images.

20. The method as recited in claim 17 in which filling the model includes:
   i) selecting a pixel grid; and
   ii) assigning an binary value to pixel locations in the finer pixel grid that substantially overlap with pixel locations contained within the model of the subject's brain.

* * * * *